United States Patent [19]

Harrison et al.

[11] 3,984,537

[45] Oct. 5, 1976

[54] ORAL PREPARATIONS

[75] Inventors: Michael Harrison, Newcastle-upon-Tyne; Kenneth Tomlinson, Bramball, both of England

[73] Assignee: Colgate-Palmolive Company, New York, N.Y.

[22] Filed: Mar. 12, 1975

[21] Appl. No.: 557,582

Related U.S. Application Data

[63] Continuation of Ser. No. 358,351, May 8, 1973, abandoned, which is a continuation of Ser. No. 143,669, May 14, 1971, abandoned.

[52] U.S. Cl. ............................ 424/54; 260/564 B; 424/326
[51] Int. Cl.² ........................................... A61K 7/22
[58] Field of Search ................... 424/54, 49–54, 424/326; 260/564 B

[56] References Cited
UNITED STATES PATENTS

| | | | |
|---|---|---|---|
| 3,562,385 | 2/1971 | Block et al. | 424/54 |
| 3,622,662 | 11/1971 | Roberts et al. | 424/54 |

FOREIGN PATENTS OR APPLICATIONS

| | | | |
|---|---|---|---|
| 702,268 | 1/1954 | United Kingdom | 260/564 B |
| 703,256 | 2/1954 | United Kingdom | 424/326 |

*Primary Examiner*—Lewis Gotts
*Assistant Examiner*—Cary Owens
*Attorney, Agent, or Firm*—Robert L. Stone; Murray M. Grill; Herbert S. Sylvester

[57] ABSTRACT

The invention relates to an oral preparation, i.e. dentifrice, which contains non-toxic amino-cyano polymeric diguanide or salt thereof as an anti-bacterial agent.

4 Claims, No Drawings

ORAL PREPARATIONS

This is a continuation, of application Ser. No. 358,351, filed May 8, 1973, which is a continuation of application Ser. No. 143,669, filed May 14, 1971, now abandoned.

This invention relates to oral preparations, i.e. preparations suitable for application to the oral cavity, including, for example, dentifrices such as toothpastes or dental creams, tooth powders and liquid dentifrices, mouthwashes or rinses, dental chewing gums, dental floss, tablets, lozenges and troches.

According to the present invention an oral preparation contains a non-toxic amino-cyano polymeric diguanide or salt thereof as an antibacterial agent, and a vehicle or carrier for the antibacterial agent and for other active ingredients (if any) present.

The amino-cyano polymeric diguanides are cationic but compatible with anionic substances and other materials such as are commonly present in oral preparations, for example, surface active agents, fluorine-providing compounds and, when the oral preparations such as a dentifrice contains a sparingly soluble polishing material, that portion of the polishing material which is water-soluble or saliva-soluble.

In one form of the invention the amino-cyano polymeric diguanide employed is prepared in accordance with a procedure substantially as set forth in British Pat. Specification No. 1,152,243. Such a procedure comprises reacting hexamethylene diamine, $H_2N(CH_2)_6NH_2$, or an inorganic salt thereof with the hexamethylene diamine salt of a dicyanimide having the formula $[H_3N-(CH_2)_6-NH_3] [N(CN)_2]$. At least the initial part of the reaction typically takes place in the presence of a hydroxylic solvent such as an aliphatic alcohol containing 1 to 4 carbon atoms, or more preferably water. The hydroxylic solvent may be mixed with a minor amount of a non-hydroxylic solvent, such as toluene. Preferably, the pH of the reaction mixutre is adjusted to about 6 to 8 with a mineral acid, such as hydrochloric acid which converts the free diamine to the acid salt, and the solution is initially heated to about 100°C at atmospheric pressure to distill off at least part of the hydroxylic solvent. The reaction mixture is then heated to about 120° to 170°C for 1 to 8 hours. Then, while cooling, water may be added if desired. The thus-obtained amino-cyano polydiguanide can then be separated from any water-immiscible solvent present and, if desired, also isolated from the aqueous solution.

The polymeric product is a mixture of polymers corresponding to the formula:

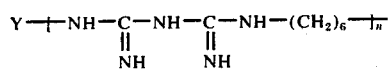

wherein Y represents $NH_2(CH_2)_6-$
or

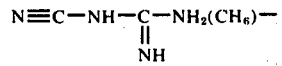

X represents $- NH_2$
or

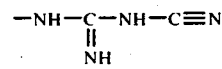

and $n$ is a low integer (e.g. 2 to 6, the average value of $n$ in the mixture being about 4).

The average molecular weight of the polymers produced by the above procedure is generally about 1100.

As already indicated, non-toxic addition salts of such compounds may be employed. Such salts may be inorganic, e.g. fluoride, chloride, nitrate or sulphate, or organic such as succinate, tartrate, citrate, maleate and methosulphate.

Certain of the addition salts are insoluble such as the water-insoluble sulphate addition salt. These salts may be incorporated into dentifrice compositions as discreet particles which may be visible on the surface of opaque dental creams or within and on the surface of visually clear, i.e. transparent or translucent, gels.

The preferred polymeric product is a mixture of various combinations of the X and Y members and various amounts of the recurring unit.

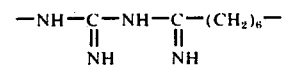

Typically the polymeric product is prepared as the chloride salt and appears to comprise mainly the linear amino-cyano polyhexamethylene diguanide:

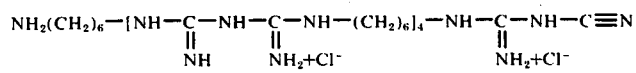

The polymer is very soluble in water and saliva and is characterized by a high degree of antibacterial activity comparable to that of 1,6-di-(p-chlorophenyl-biguanidohexane).

the polymer may be employed generally in amounts in the range from 0.01% to 5%, preferably 0.05% to 1.5%, by weight of the oral preparation.

In certain forms of the invention the oral preparation may be substantially liquid in character, such as a mouth wash or rinse. In such a preparation the vehicle is typically a water-alcohol mixture. Generally, the ratio of water to alcohol is in the range of 1:1 to 20:1, preferably 3:1 to 20:1 and most preferably about 17:3, by weight. The total amount of water-alcohol in this type of preparation is typically in the range from 70% to 99.95% by weight of the preparation. The pH of such liquid preparations is generally in the range from 4.5 to 9, typically from 5.5 to 8.

Such liquid oral preparations may also contain a surface active agent and/or a fluorine-providing compound.

In certain other forms of this invention, the oral preparation may be substantially solid or pasty in character, such as a tooth powder, or a toothpaste or dental cream. The dental vehicle of such solid or pasty oral preparations contains polishing material. Examples of polishing materials are water-insoluble sodium metaphosphate, potassium metaphosphate, tricalcium phosphate, dihydrated dicalcium phosphate, anhydrous dicalcium phosphate, calcium pyrophosphate, magnesium orthophosphate, trimagnesium phosphate, calcium carbonate, alumina, aluminum silicate, zirconium silicates, silica, plastics such as polymethyl methacrylate, bentonite and mixtures thereof. Preferred polishing material include crystalline silica having particles of sizes of up to 5 microns, a mean particle size of up to 1.1 microns and a surface area of up to 50,000 cm²/gm, insoluble sodium metaphosphate, anhydrous dicalcium phosphate and calcium carbonate which typically are finely divided to have an average particle size below 10 microns.

Alumina, particularly the hydrated alumina sold by Alcoa as C333 which has an alumina content of 64.9% by weight, a silica content of 0.008% by weight, a ferric oxide content of 0.003% and a moisture content of 0.37% at 110°C and which has a specific gravity of 2.42 and a particle size such that 100% of the particles are less than 50 microns and 84% of the particles are less than 20 microns is particularly desirable.

When visually clear gels are employed, a polishing agent of colloidal silica, such as those sold under the Trade Mark SYLOID as Syloid 72 and Syloid 74 or under the Trade Mark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus insoluble sodium metaphosphate may be formed in any suitable manner as illustrated by Thorpe's Dictionary of Applied Chemistry, Vol. 9)4th ed.), pp. 510–511. The forms of insoluble sodium metaphosphate known as Madrell's salt and Kurrol's salt are further examples of suitable materials. These metaphosphate salts exhibit a minute solubility in water, and therefore are commonly referred to as insoluble metaphosphates. There is present therein a minor amount of soluble phosphate material as impurities, usually a few percent such as up to 4% by weight. The amount of soluble phosphate material, which is believed to be a soluble sodium trimetaphosphate in the case of insoluble sodium metaphosphate, may be reduced by washing with water if desired. The insoluble alkali metal metaphosphate is typically employed in powder form of a particle size such that no more than 1% of the material is larger than 37 microns.

The polishing material is generally present in amount in the range from 20 to 99% by weight of the oral preparation. Preferably, it is present in amount in the range from 20 to 75% in toothpaste and in the range from 70 to 99% in tooth powder.

In the preparation of tooth powders, it is usually sufficient to admix mechanically, e.g., by milling, the various solid ingredients in appropriate quantities and particle sizes.

In pasty oral preparations the antibacterial diguanide polymer is compatible with the polishing material and other components of the preparation. Thus, in a toothpaste, the liquid vehicle may comprise water, typically in amount in the range from 10 to 90% by weight of the preparation. Glycerine, sorbitol or propylene glycol may also be present as humectants or binders. Particularly advantageous liquid ingredients comprise mixtures of water, glycerine and sorbitol.

In clear gels where the refractive index is an important consideration, about 10–30% by weight of water, 0 to about 80% by weight of glycerine and about 20–80% by weight of sorbitol is preferably employed. A gelling agent, such as natural or synthetic gums or gum-like materials, typically Irish moss, sodium carboxymethylcellulose, methyl cellulose or hydroxyethyl cellulose, may be employed. Other gelling agents which may be employed include synthetic inorganic silicated clay sold under the Trade Mark LAPONITE as Laponite CP and Laponite SP, having the formula $[Si_8Mg_{5.1}Li_{0.6}H_{7.6024}]^{0.6-}Na_{0.6}{}^+$, gum tragacanth, polyvinylpyrrolidone and starch. They are usually present in toothpaste in an amount up to 10% by weight, preferably in the range from 0.5% to 5%. The preferred gelling agents are methyl cellulose, hydroxyethyl cellulose, Laponite CP and most preferably Laponite SP. In a toothpaste or gel, the liquids and solids are proportioned to form a creamy or gelled mass which is extrudable from a pressurized container or from a collapsible, e.g. aluminum or lead, tube.

The solid or pasty oral preparation may also contain a surface active agent and/or a fluorine-providing compound.

Surface active agents which may be employed are organic materials and afford increased prophylactic action, and assist in achieving thorough and complete dispersion of the preparation throughout the oral cavity. The organic surface active material may be anionic, non-ionic, ampholytic or cationic in nature, and it is preferred to employ as the surface active agent a detersive material which imparts to the preparation detersive and foaming properties. Suitable such detergents are water-soluble salts of higher fatty acid monoglyceride monosulphates, such as the sodium salt of the monosulphated monoglyceride of hydrogenated coconut oil fatty acids; higher alkyl sulphates, such as sodium lauryl sulphate; alkyl aryl sulphonates, such as sodium dodecyl benzene sulphonate; higher alkyl sulphoacetates; higher fatty acid esters of 1,2-dihydroxy propane sulphonates; and substantially saturated higher aliphatic acyl amides of lower aliphatic amino carboxylic acids, such as those having 12 to 16 carbons in the fatty acid, alkyl or acyl radicals. Examples of the last mentioned amides are N-lauroyl sarcosine, and the sodium, potassium, and ethanolamide salts of N-lauroyl, N-myristyl or N-palmitoyl sarcosine. These should be substantially free from soap or similar higher fatty acid materials which tends to reduce substantially the effect of these compounds. The use of these sarcosinate compounds in dentifrice preparations of the invention is particularly advantageous since these materials exhibit a prolonged and marked effect in the inhibition of acid formation in the oral cavity due to carbohydrate breakdown, in addition to exerting some reduction in the solubility of tooth enamel in acid solutions.

Nonionic surface active agents include condensates of sorbitan monostearate with approximately 60 moles of ethylene oxides (e.g. "Tweens") condensates of ethylene oxide with propylene oxide condensates of propylene glycol ("Pluronics") and amphoteric agents such as quaternized imidazole derivatives which are available under the Trade Mark MIRANOL such as Miranol C₂M. Cationic surface active germicides and antibacterial compounds such as di-isobutylhenoxyethoxyethyl dimethyl benzyl ammonium chloride, benzyl dimethyl stearyl ammonium chloride, tertiary amines having one fatty alkyl group (of from 12 to 18 carbon atoms) and two (Poly) oxyethylene groups attached to the nitrogen (typically containing a total of from 2 to 50 ethanoxy groups per molecule) and salts thereof with acids, and compounds of the structure

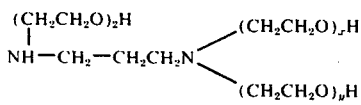

where R is a fatty alkyl group containing from 12 to 18 carbon atoms, and $x$, $y$, and $z$ total 3 or higher, as well as salts thereof with mineral or organic acids, may also be used. It is preferred to use from 0.05 to 5% by weight of surface-active material in the oral preparations.

In certain forms of this invention a fluorine-providing compound is present in the oral preparation. These compounds may be slightly soluble in water or may be fully water-soluble. They are characterized by the ability to release fluoride ions in water and by substantial freedom from reaction with other compounds of the oral preparation. Among these materials are inorganic fluoride salts, such as suitable alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride, or stannous chlorofluoride, barium fluoride, sodium fluorosilicate, ammonium fluorosilicate, sodium fluorozirconate, sodium monofluorophosphate, aluminium mono and di-fluorophosphate, fluorinated sodium calcium pyrophosphate and sodium fluorozirconate. Alkali metal and tin fluorides, such as sodium and stannous fluorides and mixtures thereof, are preferred.

The amount of the fluorine-providing compound is dependent to some extent upon the type of compound, its solubility and the type of oral preparation, but it must be a non-toxic amount. In a solid oral preparation, such as a toothpaste or tooth powder, it is considered that an amount of such compound which releases a maximum of 1% by weight, based on the weight of the preparation, of fluoride ion is satisfactory. Any suitable minimum amount of such compound may be used but it is preferable to employ sufficient compound to release from 0.005% to 1%, most preferably about 0.1%, by weight of fluoride ion. Typically, in the cases of alkali metal fluoride and stannous floride, this component is present in an amount up to 2% by weight, based on the weight of the preparation, and preferably in the range from 0.05% to 1%. In the case of sodium monofluorophosphate the compound may be present in an amount up to 7.6% by weight, typically 0.76%.

In a liquid oral preparation such as a mouth wash, the fluorine-providing compound is typically present in amount sufficient to release up to 0.13%, preferably 0.0013% to 0.1% and most preferably 0.0013% to 0.05% by weight of fluoride ion.

In certain forms of this invention an additional antibacterial agent in addition to the amino-cyano diguanide polymer may be present in amount to provide a total of about 5% by weight of antibacterial agent. Such additional agents include:

$N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1,6-di-(p-chlorophenylbiguanidohexane);
1-(lauryldimethylammonium)-8-(p-chlorobenzyldimethylammonium)octane dichloride;
5,6-dichloro-2-guanidinobenzimidazole;
$N^1$-p-chlorophenyl-$N^5$-laurylbiguanide;
5-amino-1,3-bis (2-ethylhexyl)-5-methylhexahydropyramidine; and their non-toxic acid addition salts, particularly those where the anion includes a fluorine atom, such as: fluoride, monofluorophosphate, hexafluorosilicate and hexafluoroaluminate. The dihydrogen fluoride is preferred. 1,6-di-(p-chlorophenylbiguanidohexane) dihydrogen fluoride is particularly preferred.

The total amount of antibacterial agents in the oral preparation will generally be in the range 0.01% to 5% by weight and a major amount (i.e. more than 50% by weight) of the antibacterial agent is desirably the amino-cyano diguanide polymer, and the additional antibacterial agent is present in a minor amount.

Various other materials may be incorporated in the oral preparations of this invention. Examples are coloring or whitening agents, preservatives, silicones, chlorophyl compounds and ammoniated material as urea, diammoniumphosphate and mixtures thereof. These adjuvants, where present, are incorporated in the preparations in amounts which do not substantially adversely affect the properties and characteristics desired.

Any suitable flavoring or sweetening materials may also be employed. Examples of suitable flavoring constituents are flavoring oils, e.g. oils of spearmint, peppermint, wintergreen, sassafras, clove, sage eucalyptus, marjoram, cinnamon, lemon and orange, and sodium methylsalicylate. Suitable sweetening agents include sucrose, lactose, maltose, sorbitol, sodium cyclamate, perillartine and saccharin. Suitably, flavor and sweetening agent may together comprise from 0.01% to 5% or more of the preparation.

In the manufacture of dentifrices, it is conventional to remove entrained air from the product by deaeration under vaccuum, typically at a late stage in the manufacture. In an aspect of the instant invention, it has been observed that in clear dentifrice gels of suitable viscosity, the dispersed immobile air bubbles desirably enhance the appearance of the dentifrice, and can, therefore be permitted to remain. Alternatively, the air can be replaced with another gas in non-toxic quantity, such as nitrogen or carbon dioxide. In particular, carbon dioxide can provide an effervescent character to the dentifrice.

In the event it is desired to have a minimum amount of air in the dentifrice of the instant invention, the "Unimix" apparatus described in "Process Engineering", September 11, 1970, pages 81–85, is particularly efficatious for this purpose. In this apparatus a mixing tool can be rotated in clockwise or counterclockwise manner, and the action of the mixing tool is followed by the action of a scraper blade to ensure that the working surface of the apparatus is scraped clean. Preferably a plastic such as polytetrafluorethane is used as the scraper since it is compatible with the various ingredients of the dentifrice. The positioning of the mixing tool and the scraper from a raised central column in the apparatus and the further presence of a hydraulically operated vacuum tight lid permits but little air to enter the formulation during processing. Thus, gelling agent and a portion of liquid including water and/or humectant can be efficiently blended in the Unimix apparatus. Then the remaining water and liquid can be separately blended with the polishing agent and additional components (except for post-added components, such as flavoring oil) in the Unimix, and then the two dispersions blended together in the Unimix apparatus. If desired, the small amount of air can be largely removed under the depressurized conditions in the apparatus. The apparatus can be used to blend ingredients at room temperature as well as at higher temperatures.

The following Examples illustrate the invention. The ingredients are mixed in the usual manner. Percentages are by weight. The polymeric diguanide is prepared according to the procedure described in British Pat. Specification No. 1,152,243.

EXAMPLE 1

| Mouth-rinse | % |
|---|---|
| Ethanol | 15.0 |
| "Pluronic 75" | 0.5 |
| Sodium fluoride | 0.05 |
| Polymeric diguanide | 0.1 |
| Sodium saccharin | 0.2 |
| Flavor/Color | 1.0 |
| Water | To 100.0 |

EXAMPLE 2

| Mouth-rinse | % |
|---|---|
| Ethanol | 4.0 |
| Glycerol | 1.0 |
| Sodium monofluorophosphate | 0.2 |
| Polymeric diguanide | 0.5 |
| "Tween 80" | 0.5 |
| Sodium saccharin | 0.2 |
| Flavor/Color | 1.0 |
| Water | To 100.0 |

EXAMPLE 3

| Dentifrice | % |
|---|---|
| Hydrated alumina | 55.0 |
| Glycerine | 20.0 |
| Hydroxyethyl cellulose | 1.0 |
| "Miranol C₂M" | 1.0 |
| 1,6-di-p-(Chlorophenyl biguanidohexane) | 0.20 |
| Polymeric diguanide | 0.25 |
| Sodium saccharin | 0.2 |
| Flavor | 1.0 |
| Water | To 100.0 |

EXAMPLE 4

| Dentifrice | % |
|---|---|
| Dicalcium phosphate dihydrate | 40.0 |
| Calcium carbonate (precipitated) | 8.0 |
| Glycerine | 10.0 |
| Sorbitol (70%) | 12.0 |
| Sodium N-lauroyl sarcosinate | 2.0 |
| Carboxymethylcellulose | 0.9 |
| Sodium benzoate | 0.2 |
| Tetrasodium pyrophosphate | 0.5 |
| Sodium saccharin | 0.2 |
| Flavor | 1.0 |
| Polymeric diguanide | 0.5 |
| Water | To 100.0 |

EXAMPLE 5

| Dentifrice | % |
|---|---|
| Crystalline silica | 20.0 |
| Polymethyl methacrylate | 20.0 |
| Glycerol | 20.0 |
| Sodium lauroyl sulphate | 2.0 |
| Hydroxyethyl cellulose | 1.0 |
| Sodium fluoride | 0.1 |
| Polymeric diguanide | 0.5 |
| Sodium saccharin | 0.2 |
| Flavor | 1.0 |
| Water | To 100.0 |

EXAMPLE 6

| Dentifrice | % |
|---|---|
| Insoluble sodium metaphosphate | 45.0 |
| Glycerol | 6.0 |
| Sorbitol | 16.0 |
| Sodium N-lauroyl sarcosinate | 2.0 |
| Sodium monofluorophosphate | 0.8 |
| Polymeric diguanide | 0.5 |
| Hydroxyethyl cellulose | 1.0 |
| Sodium saccharin | 0.2 |
| Flavor | 1.0 |
| Water | To 100.0 |

EXAMPLE 7

| Dentifrice | % |
|---|---|
| Calcium carbonate (calcitic) | 20.0 |
| Calcium carbonate (aragonitic) | 25.0 |
| Glycerol | 20.0 |
| "Pluronic 75" | 1.0 |
| Polymeric diguanide | 0.25 |
| 1,6-di-p-(Chlorophenyl biguanidohexane) | 0.20 |
| Sodium saccharin | 0.2 |
| Sodium carboxymethylcellulose | 1.0 |
| Water | To 100.0 |

We claim:

1. A dentifrice comprising about 0.01-5% by weight of a water-soluble non-toxic amino-cyano polymeric diguanide as antibacterial agent wherein said antibacterial agent is a mixture of the monofluorophosphate salt of an amino-cyano polymeric diguanide having the formula:

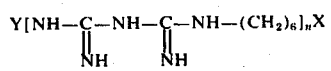

wherein Y is selected from the group consisting of

and

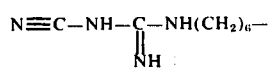

X is selected from the group consisting of —NH₂ and

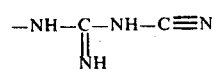

and $n$ is an integer 2-6, and a dental vehicle for said agent compatible therewith, containing a solid water-insoluble polishing material.

2. A dentifrice comprising about 0.01-5% by weight of a water-soluble non-toxic amino-cyano polymeric diguanide as antibacterial agent wherein said antibacterial agent is a mixture of the carbonate salt of an amino-cyano polymeric diguanide having the formula:

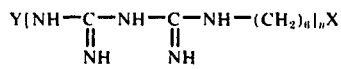

wherein Y is selected from the group consisting of

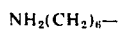

and

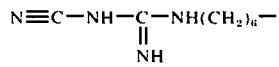

X is selected from the group consisting of
—NH$_2$
and

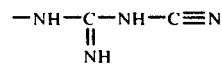

and $n$ is an integer 2-6, and a dental vehicle for said agent compatible therewith, containing a solid water-insoluble polishing material.

3. An oral preparation comprising about 0.01-5% by weight of a water-soluble non-toxic amino-cyano polymeric diguanide as antibacterial agent wherein said antibacterial agent is a mixture of the phosphate salt of an amino-cyano polymeric diguanide having the formula:

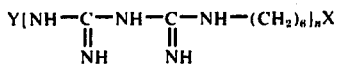

wherein Y is selected from the group consisting of
NH$_2$(CH$_2$)$_6$—
and

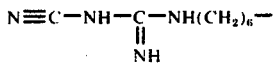

X is selected from the group consisting of
—NH$_2$
and

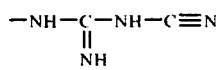

and $n$ is an integer 2-6, and a dental vehicle for said agent compatible therewith, containing a water-insoluble polishing material.

4. The dentifrice claimed in claim 1 wherein the polymer mixture is mainly the monofluorophosphate salt of

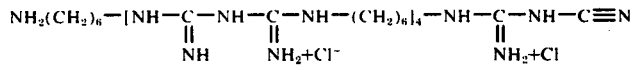

* * * * *